United States Patent [19]
Peterson

[11] Patent Number: 5,882,320
[45] Date of Patent: Mar. 16, 1999

[54] DISPOSABLE CAST OR BANDAGE PROTECTOR

[76] Inventor: Lloyd E. Peterson, 13205 Lakeview Dr., Burnsville, Minn. 55337

[21] Appl. No.: 890,704

[22] Filed: Jul. 11, 1997

[51] Int. Cl.⁶ .................................. A61F 5/00; A61F 5/37
[52] U.S. Cl. ................................................ 602/3; 128/876
[58] Field of Search .............................. 602/3, 4, 57, 60, 602/65, 19; 128/876; 604/345, 353; 396/25, 27; 383/70, 71; 24/30.5 P, 306

[56] References Cited

U.S. PATENT DOCUMENTS

| | | | |
|---|---|---|---|
| 949,716 | 2/1910 | Quenzer | 602/60 |
| 3,747,125 | 7/1973 | Goldman et al. | |
| 3,973,610 | 8/1976 | Ballin | 24/30.5 P |
| 4,008,851 | 2/1977 | Hirsch | 24/30.5 P |
| 4,215,687 | 8/1980 | Shaw | 602/60 |
| 4,254,765 | 3/1981 | Brown et al. | |
| 4,363,317 | 12/1982 | Broucek | |
| 4,414,969 | 11/1983 | Heyman | 128/882 X |
| 4,422,455 | 12/1983 | Olsen | 128/882 X |
| 4,523,586 | 6/1985 | Couri | |
| 4,562,834 | 1/1986 | Bates et al. | |
| 4,727,864 | 3/1988 | Wiesenthal et al. | |
| 4,911,151 | 3/1990 | Rankin et al. | |
| 5,111,807 | 5/1992 | Spahn et al. | 602/19 X |

*Primary Examiner*—Richard J. Apley
*Assistant Examiner*—Denise Pothier
*Attorney, Agent, or Firm*—James W. Miller

[57] ABSTRACT

A cast or bandage protector comprises a lightweight, plastic bag having a rectangular shape that is open at one end. The user can insert an arm or leg through the open end of the bag to protect a cast or bandage from getting wet. A strap encircles the bag adjacent the open end thereof. The strap is also made of plastic and has a buckle at one end that is free relative to the bag to allow access to be had to the underside of the buckle. The other free end of the strap can be threaded through the buckle and cinched back on itself to tighten the strap, and hence the open end of the bag, around the arm or leg of the user. The free end of the strap is secured in place by an adhesive patch that is pressed against the strap or bag. The protector is disposed of after a single use by stripping the protector off the arm or leg and throwing it away.

7 Claims, 2 Drawing Sheets

DISPOSABLE CAST OR BANDAGE PROTECTOR

TECHNICAL FIELD

This invention relates to a protector for enclosing and covering a cast or bandage on a user's arm or leg to prevent the cast or bandage from getting wet while taking a shower or bath. More particularly, this invention relates to a protector comprising a flexible, plastic bag that can be easily applied using only one hand and that is inexpensive to be disposable after one use.

BACKGROUND OF THE INVENTION

Protective devices are known which comprise elongated sheathes or bags that fit around the arm or leg of a user to cover a cast or bandage that has been applied to the arm or leg. The protector prevents the cast or bandage from getting wet. As such, it is used primarily when the user is bathing in a bath or shower. However, it is not limited to that use, but could also be worn while the user is outside to prevent rain from reaching the cast or bandage.

Certain protectors of the prior art comprise bags that, are closed at one end and open at the other end. A strap is attached to the bag near the open end of the bag. The strap carries a buckle at one end. The other end of the strap is, free to be inserted through the buckle.

In using these protectors, the user inserts whatever limb has the cast or bandage into the bag until the cast or bandage is located within the bag. The user then threads the free end of the strap through the buckle and pulls back on the free end of the strap to cinch the strap tight. The free end of the strap is then secured in place using Velcro fasteners. U.S. Pat. No. 3,747,125 to Goldman and U.S. Pat. No. 4,254,765 to Brown show such bags having buckle carrying straps adjacent the open end of the bag.

While the protectors shown in the above described patents are useful, they are quite expensive and are not adapted to a single use. For example, the closed end of the bags mimic the shape of a hand or foot. This requires that pieces of plastic material first be cut with the necessary shape. The protectors are then finished by assembling the cut pieces together, i.e. by securing the pieces to each other along their edges. The expense involved in this cutting and assembly greatly increases the cost of these protectors.

In addition, the securing straps used in these protectors are often made of a fabric material that is sewn or otherwise attached to the bags. Moreover, Velcro material is used to fasten the straps in place after the straps are tightened. This Velcro material is itself expensive. Accordingly, due to the expense involved in manufacturing and selling such protectors, they are not truly disposable after a single use. These protectors have never been commercialized to the best of the Applicant's knowledge.

Since the expense of these protectors dictates trying to reuse them, the user would normally try and remove the protectors and keep them until a future time when they might. be needed again. However, this is not a good solution due to the need for such protectors to dry thoroughly and because of the possibility of bacterial or other contamination after their first use. Thus, as a practical matter, such protectors would not be reused. They are simply too expensive to constitute a product that can be disposed after a single use.

U.S. Pat. No. 4,911,511 to Rankin attempts to provide a disposable protector having a strap for tightening the open end of the bag. Rankin teaches using a plastic strap without a buckle instead of the buckle carrying straps of the Goldman or Brown protectors. In addition, the free end of the Rankin strap is secured by adhesive rather than by Velcro fasteners. While this would potentially decrease the cost of the Rankin protector, the lack of a buckle on a simple plastic type strap decreases its utility and makes one handed application very difficult.

Without a buckle, the Rankin strap cannot be cinched back on itself. Thus, when force is applied to the end of the strap, such force would often simply tend to rotate the entire protector around the limb without tightening the strap. The Rankin strap could probably be tightened adequately by a user having two hands such as when the protector is placed over a cast on the user's leg. But, when the user has only one hand to use, such as when the protector is placed over the user's other arm, the tendency of the bag to slide around the arm when the user tightens the strap is a great disadvantage. The Rankin protector is not. suited for one handed application.

SUMMARY OF THE INVENTION

One aspect of this invention is to provide a cast or bandage protector that is suited for being easily applied and tightened by a user having only one hand to use and that is disposable after a single use.

These and other aspects of this invention are provided by a cast or bandage protector for covering an arm or leg of a user. The protector comprises an elongated, flexible, plastic bag forming and enclosure and having an open end into which the arm or leg of the user can be inserted until the arm or leg is contained at least partly within the bag. A flexible, plastic strap is carried adjacent the open end of the bag for cinching the open end of the bag shut against the arm or leg of the user. The strap is elongated and extends between a first end having a buckle and a second free end. An adhesive patch is carried on the second free end of the strap on a surface of the strap that faces the bag after the free end of the strap is inserted through the buckle and pulled back on itself in a cinching type action. The adhesive patch is sufficiently sticky to adhere the strap to itself or the bag to hold the bag closed after the strap has been cinched.

BRIEF DESCRIPTION OF THE DRAWINGS

This invention will be described more completely in the following Detailed Description, when taken in conjunction with the following drawings, in which like reference numerals refer to like elements throughout.

DETAILED DESCRIPTION

Figure 1:
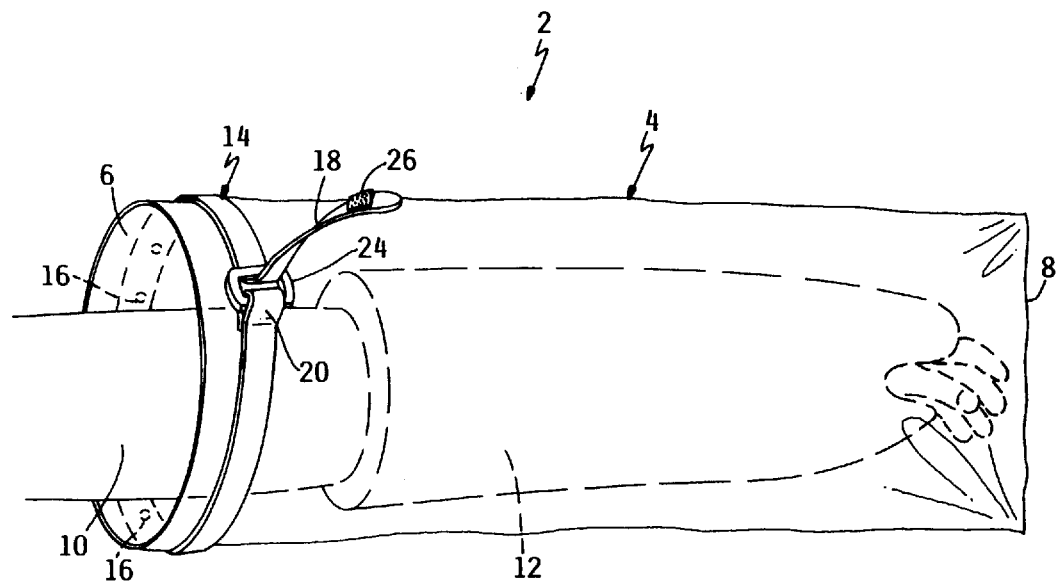
FIG. 1 is a perspective view of a cast or bandage protector according to this invention as applied to a user's arm and after the strap has been inserted through the buckle but before the strap is tightened, the protector being shown in FIG. 1 having a first embodiment of the tightening strap.

The cast or bandage protector of this invention is generally illustrated as 2 in FIG. 1. Protector 2 comprises an elongated sheath or bag 4 that is substantially enclosed over its entire surface except for one open end 6. The other end 8 of bag 4 opposite to open end 6 is closed. Bag 4 thus forms a tubular enclosure into which the user can insert a limb of his body, such as an arm or leg 10, which carries a cast or bandage 12.

Bag 4 encloses cast or bandage 12 protects it from getting wet while the user is taking a bath or shower. It can also be employed when the user is engaged in other activities that might cause cast or bandage 12 to become wet. Moreover, bag 4 protects cast or bandage 12 from contaminants other than water, and so might also be worn at other times and places.

Bag 4 is sized to comfortably fit around arm or leg 10 of a person. Bags of different lengths could be provided to accommodate the natural variation in the arm or leg lengths of different users. For example, bag 4 could be sold in small, medium or large versions. In any event, each user would purchase a protector 2 in which bag 4 is long enough to cover his or her's own particular arm or leg.

A lightweight, flexible plastic material, such as the types of plastic materials used to make household garbage or trash bags, is preferably used to make bag 4. This material is impervious to water and other contaminants, but is so inexpensive that protector 2 can be thrown away after a single use. Bag 4 preferably has a simple rectangular shape so that it can be inexpensively mass produced in a continuous manner. For example, the plastic material could be extruded in a continuous form and then cut apart at intervals to form bag 4 with the closed end 8 of bag 4 being heat sealed, together. There are no specially shaped pieces or separate pieces that have to be overlaid and secured together in bag 4.

A means is provided adjacent open end 6 of bag 4 for tightly cinching open end 6 of bag 4 around the user's arm or leg. This cinching means comprises a tightening strap, indicated generally as 14. An important part of this invention is to make tightening strap 14 from the same or similar types of plastic materials used to make bag 4. Thus, strap 14 can also be inexpensively provided in keeping with the disposable, single use nature of protector 2. However, strap 14 is designed to be secured by a user using only a single hand if need be.

Figure 2:
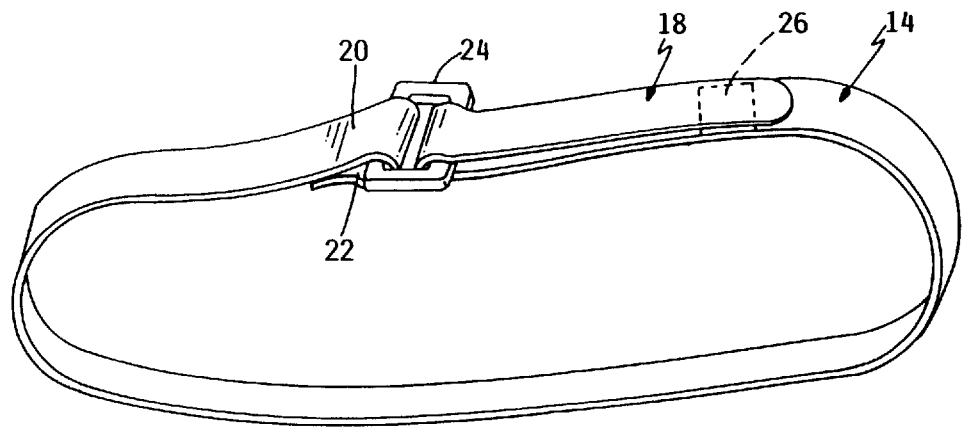
FIG. 2 is an enlarged perspective view of the first embodiment of the tightening strap shown in FIG. 1.

Referring to the first embodiment of strap 14 shown in FIGS. 1 and 2, strap 14 is elongated having a generally constant width. Most of the length of strap 14 intermediate its ends is fixed securely to bag 4 by any suitable means. For example, strap 14 could be secured at spaced locations to bag 4 by small patches 16 of adhesive or the like. However, the entire length of strap 14 is not secured to bag 4 by such adhesive patches 16. At least one end 18 of strap 14 needs to be free from bag 4 over a length of at least several inches to allow strap 14 to be tightened to cinch open end 6 of bag 4 closed.

One end 20 of strap 14 is bent back around and secured to itself to form a loop 22 that carries an inexpensive plastic buckle 24. Buckle 24 is permanently carried on strap 14 as the one end 20 of strap 14 is inserted through buckle 24 as loop 22 is being formed and before strap 14 is secured to itself to form loop 22. Buckle 24 is free to move relative to bag 4, in effect pivoting or rotating around in loop 22. This gives buckle 24 enough freedom of motion to allow the other free end 18 of strap 14 to be threaded through buckle 24 before strap 14 tightened.

The other free end 18 of strap 14 can be inserted through buckle 24 and then pulled back on itself in a cinching type action to tighten open end 6 of bag 4 around arm or leg 10 of the user. Referring to FIG. 1, strap 14 is shown with its free end inserted up through buckle 24, but before strap 14 has been pulled back on itself in a cinching action. FIG. 2 shows strap 14 after the cinching action is complete and strap 14 is tightened. However, the rest of bag 4 has been deleted from FIG. 2 only for the purpose of clarity.

It is not enough that strap 14 can be inserted through buckle 24 and then cinched back on itself. Some means must be provided to keep strap 14 in this tightened or cinched position to keep bag 4 from loosening during use. It is preferred that this means comprise a small patch 26 of adhesive or pressure sensitive sticky tape located on the upper surface of free end 18 of strap 14. This adhesive patch 26 effectively becomes located on the lower surface of free end 18 of strap 14 after strap 14 is inserted onto buckle 24 and is cinched back on itself. This adhesive patch can simply be pressed inwardly onto strap 14 or some portion of bag 4 after strap 14 has been tightened to lock or secure free end 18 of strap 14 to bag 4.

The use of an adhesive patch 26 is preferred because it again does not increase the cost of protector 2 substantially. Adhesives that would be suitable for this purpose are quite well known and it is contemplated that a quite sticky adhesive would be used, so much so that strap 14 once secured in place could not be disengaged without ripping or destroying bag 4. To prevent contact with adhesive patch 26 prior to use, patch 26 would normally be covered with a peel off film 28 to prevent inadvertent adhesion of patch 26 to various surfaces. Film 28 is not shown in FIGS. 1 and 2, but is illustrated as 28' and 28" in the embodiments of strap 14 shown in FIGS. 3 and 4.

In using protector 2 of FIGS. 1 and 2, protector 2 would be sold in a flat, collapsed condition in some type of appropriate packaging. The user who wishes to use protector 2 would unfold or expand protector 2 until access was had to open end 6 of protector 2. The user would then insert the appropriate limb into protector 2 through open end 6 until cast or bandage 12 was inside protector 2 and protected by bag 4 of protector 2.

It is then necessary to tighten or cinch strap 14 to secure protector 2 in place. The user would grab free end 18 of strap 14 and thread it up through buckle 24 much as is shown in FIG. 1. The protective peel off film 28 would then be removed from adhesive patch 26 to uncover adhesive patch 26 for use. The user would then pull back on free end 18 of strap 14 to draw it through buckle 24 in a cinching type action. After strap 14 is sufficiently tight to secure or hold protector 2 in place, free end 18 of strap 14 would then simply be pressed against either some portion of strap 14 or bag to secure or lock strap 14 in place.

In order to ease the task of pulling back on strap 14 without the user's fingers contacting adhesive patch 26, free end 18 of strap 14 could also be formed with a loop 30 large enough to receive at least one of the user's fingers. Thus, the user could insert a finger through loop 30 when pulling back on or otherwise manipulating free end 18 of strap 14. This would keep the user's fingers and hand out of the way of adhesive patch 26. Such a finger loop 30 is shown only in the strap embodiment of FIG. 4 as 30". While such a finger loop 30 could be used on free end 18 of strap 14, it could also be dispensed with as shown in the strap embodiment of FIGS. 1–2.

After protector 2 has served its intended purpose, e.g. protecting cast or bandage 12 while taking a shower or bath, it can be easily removed by cutting or ripping it off. Because bag 4 that forms protector 2 is formed of a lightweight plastic material, and strap 14 is also formed of the same or similar type of material with an inexpensive plastic buckle 24 and adhesive fastener patch 26, protector 2 can simply be thrown away after a single use. Thus, protector 2 of this invention is the first truly disposable cast or bandage protector that is still easy to apply and use. Use of a buckle carrying strap 14 ensures that protector 2 can be properly installed and tightened using only one hand.

Figure 3:
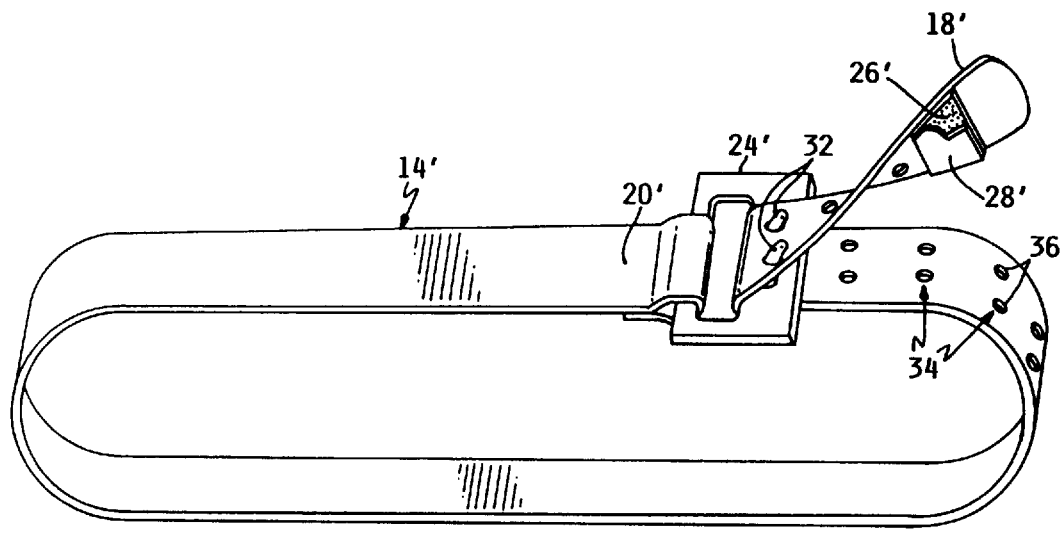
FIG. 3 an enlarged perspective view of a second embodiment of the tightening strap which can be used on the cast. or bandage protector of FIG. 1 in place of the first embodiment of the strap shown in FIG. 1.
Figure 4:
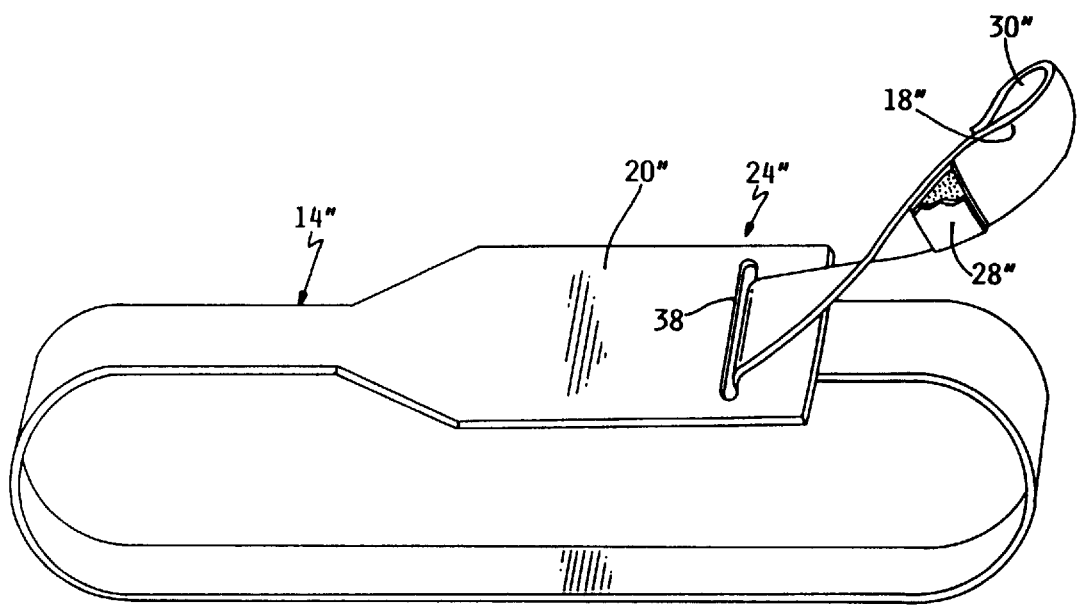
FIG. 4 an enlarged perspective view of a third embodiment of the tightening strap which can be used on the cast: or bandage protector of FIG. 1 in place of the first embodiment of the strap shown in FIG. 1.

The embodiments of FIGS. 3 and 4 show different embodiments of tightening strap 14 that can be used in place of strap 14 shown in FIGS. 1 and 2. To the extent straps 14 of FIGS. 3 and 4 are similar or the same as strap 14 shown in FIGS. 1 and 2, the same reference numeral will apply with a prime or double prime suffix. Thus, the strap of FIG. 3 will be identified as 14', while the strap of FIG. 4 will be identified as 14".

Referring now to FIG. 3, strap 14' differs from strap 14 in that plastic buckle 24 has at least one, and preferably two, upwardly extending prongs 32. Free end 18' of strap 14' is provided with sets 34 of double perforations 36 that are adapted to be secured on prongs 32 much in the manner of a belt. Thus, the connection formed by prongs 32 and perforations 36 serves to additionally secure strap 14' in its tightened condition. The sets 34 of perforations 36 extend over free end 18' of strap 14' for a distance sufficient to engage prongs 32 over the amount of contraction of open end 6 of bag 4 that would be encountered during use of bag 4.

Strap 14" of FIG. 4 does not use a separate buckle 24 secured to the one end 20" of strap 14" by a buckle carrying loop. Instead, the one end 20" of strap 14" is formed as a wider portion than the rest of strap 14" and buckle 24" is formed merely by a slot 38 cut into the wider one end 20" of strap 14. The wider one end 20" strap 14 would not be affixed to bag 4, but would be free so that access could be had to buckle 24" formed by slot 38. If desired, the wider one end 20" of strap 14" could be made of a thicker and stiffer piece of plastic than the remaining portions of strap 14" which is adhesively secured or welded to the remaining portions of strap 14". Strap 14" is likely to be the lowest cost strap since a separate plastic buckle 24 is not needed.

Another way of forming a usable buckle 24 would be to simply make loop 22 on the one end 20 of strap 14 large enough to allow free end 18 to be threaded through loop 22 without using the separate plastic buckle 24 at all. It is preferred that buckles 24 of the type shown in FIGS. 1 and 4 be used since strap 14 can be threaded through such buckles 24 without twisting. However, a simple loop 24 on the one end 20 of strap 14 would suffice even if strap 14 twists passing through it.

Various other modifications of this invention will be apparent to those skilled in the art. Thus, the scope of the invention shall be limited only by the appended claims.

I claim:

1. A cast or bandage protector for covering an arm or leg of a user, which comprises:

(a) an elongated, flexible, plastic bag forming and enclosure and having an open end into which the arm or leg of the user can be inserted until the arm or leg is contained at least partly within the bag;

(b) a flexible plastic strap permanently carried on the bag as part of the bag and being located adjacent the open end of the bag for cinching the open end of the bag shut against the arm or leg of the user, wherein the strap is elongated and extends between a first end having a buckle and a second free end, wherein the first end of the strap carrying the buckle is unattached to the bag to allow access to be had to the buckle such that the second free end of the strap can be threaded through the buckles wherein the buckle is an integral portion of the strap with the buckle and the strap being formed as a single, integrally molded piece;

(c) an adhesive patch carried on the second free end of the strap on a surface of the strap that faces the bag after the free end of the strap is inserted through the buckle and pulled back on itself in a cinching type action, the adhesive patch being made of a pressure sensitive and inherently sticky adhesive material that adheres the strap in place simply by pressing the adhesive patch into contact with the strap or the bag to hold the bag closed after the strap has been cinched;

(d) wherein the adhesive patch is covered by a protective peel-off film that is carried on the free end of the strap with the film overlying the adhesive patch to prevent inadvertent adhesion of the adhesive patch at undesired locations or to unwanted surfaces, and wherein the free end of the strap, the adhesive patch and the protective peel-off film are collectively sufficiently thin and so located as to allow the free end of the strap including the adhesive patch and the protective peel-off film to be inserted through the buckle before the protective peel-off film is removed from the adhesive patch; and (e) wherein the second free end of the strap has a portion which is shaped to allow the user to grip and pull on the second free end of the strap after the protective peel-off film is removed from the adhesive patch without contacting the adhesive patch.

2. The protector of claim 1, wherein the buckle is formed as a slot in the first end of the strap with the portions of the strap immediately adjacent the slot being unattached to the bag to allow access to the slot.

3. The protector of claim 2, wherein the first end of the strap is wider than the free end of the strap, and wherein the slot that forms the buckle is wider than the free end of the strap to allow the free end of the strap to be inserted through the slot.

4. The protector of claim 1, wherein the portion of the strap on the second free end of the strap which the user can grip and pull comprises a loop formed as part of an outermost tip of the free end of the strap.

5. The protector of claim 4, wherein the loop is formed by bending back a portion of the free end of the strap onto itself and securing the bent back portion of the strap to the strap.

6. The protector of claim 5, wherein the loop is sized to receive one of the user's fingers.

7. The protector of claim 1, wherein the adhesive patch and protective peel-off film cover only a small portion of the length of the strap at the second free end of the strap.

* * * * *